United States Patent
St. Pierre

(10) Patent No.: US 10,296,965 B2
(45) Date of Patent: May 21, 2019

(54) DEVICE CONFIGURATION

(71) Applicant: Welch Allyn, Inc., Skaneateles Falls, NY (US)

(72) Inventor: Shawn C. St. Pierre, Syracuse, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 1192 days.

(21) Appl. No.: 14/535,576

(22) Filed: Nov. 7, 2014

(65) Prior Publication Data

US 2016/0132957 A1   May 12, 2016

(51) Int. Cl.
| | |
|---|---|
| G06Q 30/06 | (2012.01) |
| G06F 9/445 | (2018.01) |
| A61B 5/00 | (2006.01) |
| A61B 5/01 | (2006.01) |
| A61B 5/021 | (2006.01) |
| A61B 5/08 | (2006.01) |
| A61B 5/145 | (2006.01) |

(52) U.S. Cl.
CPC ........... *G06Q 30/0635* (2013.01); *A61B 5/01* (2013.01); *A61B 5/021* (2013.01); *A61B 5/7475* (2013.01); *G06F 9/44505* (2013.01); *A61B 5/0816* (2013.01); *A61B 5/14542* (2013.01); *A61B 2562/12* (2013.01)

(58) Field of Classification Search
CPC .................................. G06Q 30/0601–30/0645
USPC ................................................ 705/26.1–27.2
See application file for complete search history.

(56) References Cited

U.S. PATENT DOCUMENTS

| | | |
|---|---|---|
| 6,003,012 A | 12/1999 | Nick |
| 6,493,677 B1 | 12/2002 | von Rosen et al. |
| 6,882,982 B2 | 4/2005 | McMenimen et al. |
| 7,013,290 B2 | 3/2006 | Ananian |
| 7,016,865 B1 | 3/2006 | Weber et al. |
| 7,216,092 B1 | 5/2007 | Weber et al. |
| 7,627,503 B1 | 12/2009 | Champagne et al. |
| 7,890,870 B1 | 2/2011 | Metters et al. |
| 9,471,752 B2 * | 10/2016 | Goetz ................. G06F 19/3418 |
| 2002/0007294 A1 | 1/2002 | Bradbury et al. |
| 2002/0103505 A1 | 8/2002 | Thompson |
| 2003/0009354 A1* | 1/2003 | Arbogast ............... G06Q 10/06 705/2 |
| 2003/0115108 A1 | 6/2003 | Scott et al. |

(Continued)

FOREIGN PATENT DOCUMENTS

| | | |
|---|---|---|
| KR | 1020070018341 A | 2/2007 |
| WO | WO 01/33464 A1 | 5/2001 |
| WO | WO 01/80739 A1 | 11/2001 |

OTHER PUBLICATIONS

International Search Report and Written Opinion for PCT/US2015/059435, dated Feb. 17, 2016, 12 pages.

(Continued)

*Primary Examiner* — Nicholas D Rosen
(74) *Attorney, Agent, or Firm* — Merchant & Gould P.C.

(57) ABSTRACT

A system and method for configuring a device include determining a plurality of configuration settings for the device. The configuration settings are saved in a configuration file, and a sales order for the device is generated. The configuration file is assigned to the sales order. Based on the sales order, the configuration file is retrieved and applied to the configuration settings to the device.

12 Claims, 15 Drawing Sheets

(56) References Cited

U.S. PATENT DOCUMENTS

| | | | |
|---|---|---|---|
| 2005/0144528 A1 | 6/2005 | Bucher et al. | |
| 2006/0253789 A1* | 11/2006 | Cobb | G06F 17/50 |
| | | | 715/762 |
| 2007/0118431 A1* | 5/2007 | Johansson | G06Q 30/06 |
| | | | 705/26.5 |
| 2008/0141217 A1* | 6/2008 | Goetz | G06F 19/3418 |
| | | | 717/111 |
| 2009/0063187 A1* | 3/2009 | Johnson | A61B 5/411 |
| | | | 705/2 |
| 2009/0171175 A1 | 7/2009 | Li et al. | |
| 2011/0071420 A1 | 3/2011 | St. Pierre et al. | |
| 2011/0245630 A1 | 10/2011 | St. Pierre et al. | |
| 2012/0296183 A1 | 11/2012 | Kinsley et al. | |
| 2013/0245467 A1 | 9/2013 | St. Pierre et al. | |
| 2014/0156812 A1 | 6/2014 | Deng et al. | |
| 2014/0288950 A1* | 9/2014 | Park | G06Q 10/10 |
| | | | 705/2 |
| 2014/0337152 A1* | 11/2014 | Renaldi | G06Q 20/203 |
| | | | 705/22 |
| 2015/0378798 A1* | 12/2015 | Gondek | G06F 9/44505 |
| | | | 719/313 |
| 2016/0203304 A1* | 7/2016 | Bielstein | G06F 3/048 |
| | | | 715/741 |

OTHER PUBLICATIONS

Tudjarov, B. et al., "Web Virtual Reality for Product Customization," Advances in Production Engineering & Management, vol. 4, 1 special, pp. 25-34 (2009).

* cited by examiner

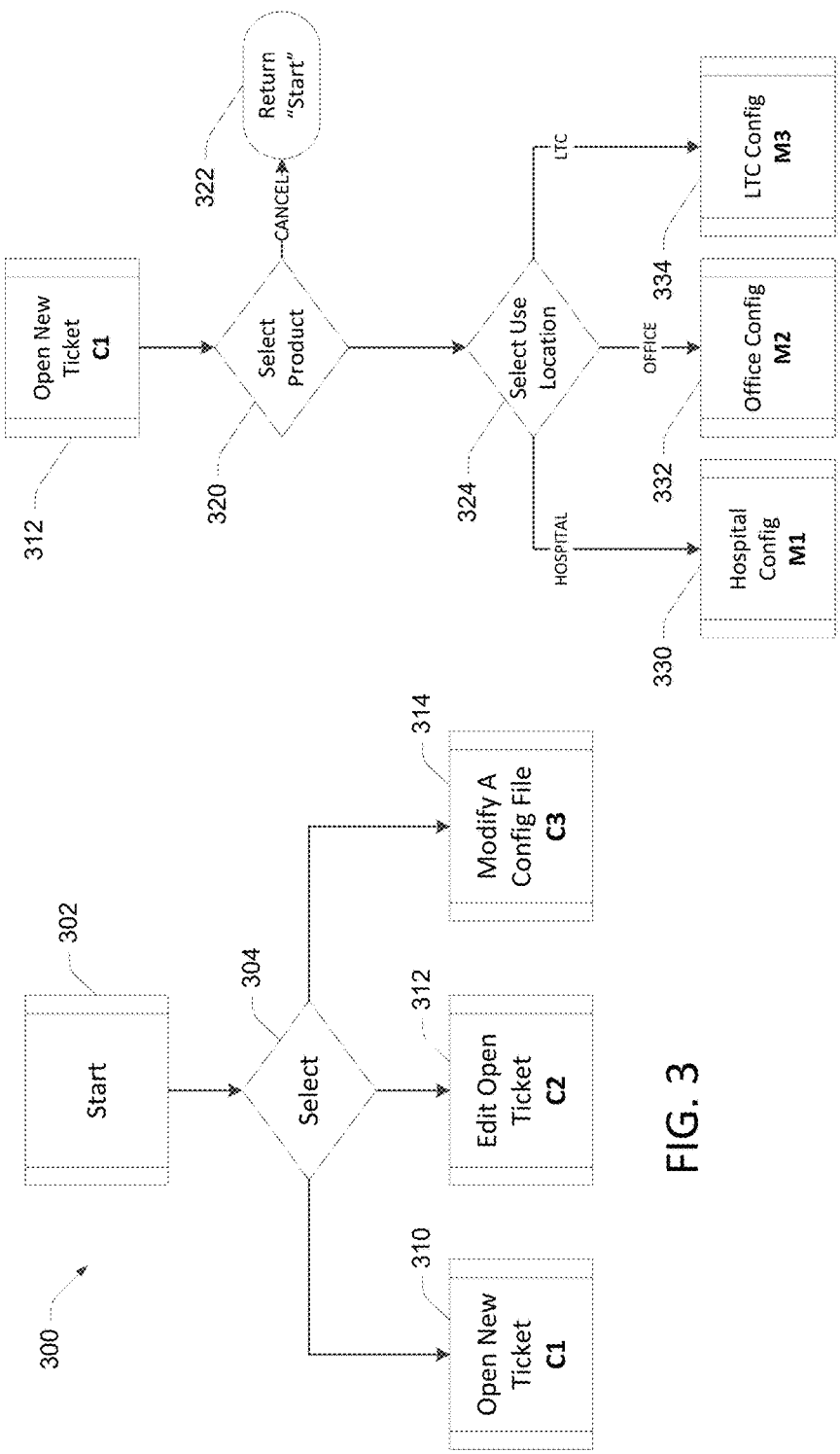

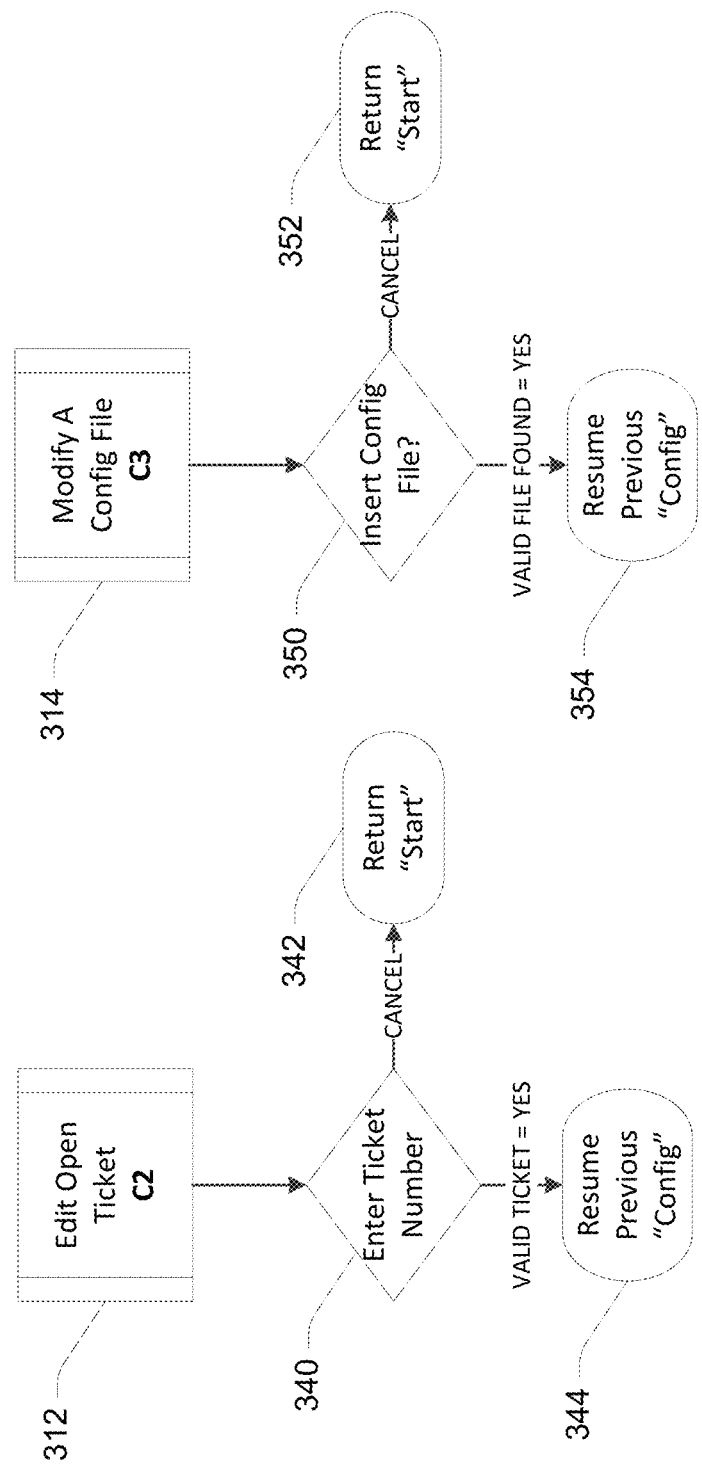

DEVICE CONFIGURATION

BACKGROUND

Computerized devices, such as some medical monitoring devices, often require configuring many parameters so that the device functions in the manner desired by the user. Typically, a "generic" hardware device is manufactured, and then the device is configured at a user site by the user or a technician. For example, health care practitioners, such as nurses or physicians, use various types of health-care equipment to assist with the task of providing health care to a patient, also referred to herein as a health-care recipient. Some health-care equipment includes one or more modules that are designed to perform one or more functions, such as temperature measurement, blood pressure measurement, oxygen level measurement, etc. Additionally, many software settings are provided that determine device management and security, data transmission, parameter defaults, interval timing, etc. Providing many varied configuration settings allows a device to function in many different ways, providing flexibility to the user. However, such increased configurability also can add complexity to the device set up process.

SUMMARY

In accordance with aspects of the present disclosure, a system and method for configuring a device include determining a plurality of configuration settings for the device. In some embodiments, the device is a vital signs monitor. The configuration settings are saved in a configuration file, and a sales order for the device is generated. The configuration file is assigned to the sales order. Based on the sales order, the configuration file is retrieved and applied to the configuration settings to the device.

BRIEF DESCRIPTION OF THE DRAWINGS

Non-limiting and non-exhaustive embodiments are described with reference to the following Figures.

FIG. 3 is a flow diagram illustrating a further example of a configuration process in accordance with aspects of the present disclosure.

FIG. 4 is a flow diagram illustrating further aspects of the configuration process shown in FIG. 3.

FIG. 5 is a flow diagram illustrating further aspects of the configuration process shown in FIG. 3.

FIG. 6 is a flow diagram illustrating further aspects of the configuration process shown in FIG. 3.

DETAILED DESCRIPTION

In the following detailed description, references are made to the accompanying drawings that form a part hereof, and in which are shown by way of illustrations specific embodiments or examples. These aspects may be combined, other aspects may be utilized, and structural changes may be made without departing from the spirit or scope of the present disclosure. The following detailed description is therefore not to be taken in a limiting sense.

Many different types of devices require a configuration process in which various parameters are set so that the device functions as desired. Often, a "generic" device is manufactured, and then hardware and software settings are configured as required for the particular implementation of the device, effectively resulting in a "customized" device. In some situations, it could be desirable to configure such a device during the manufacturing process, prior to shipping the device from the factory. However, this could complicate the manufacturing process. For example, a given device is typically assigned a part number. Producing such devices with a configuration customized for each end user could necessitate assigning unique part numbers for each configured device.

Figure 1:
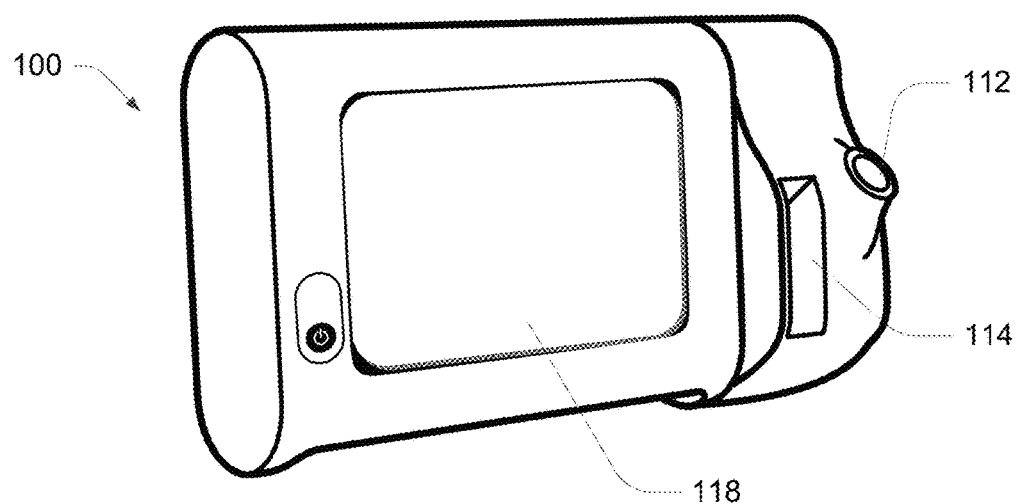
FIG. 1 is a perspective view of a configurable device suitable for being configured according to disclosed configuration methods and systems.

For example, certain medical devices, such as vital signs measurement and/or monitoring devices, often include many hardware and software settings. FIG. 1 illustrates an example of a medical device 100 that can be configured to measure and monitor a variety of patient parameters. The illustrated medical device 100 is functionally connected to one or more sensors that enable monitoring of at least one physiological parameter associated with a patent. Typically, each sensor is physically attached to the patient while the device 100 is operating to acquire measurements of a parameter associated with the sensor.

The medical device 100 includes a user interface 118, such as a touch screen, and includes the ability to execute multiple workflows or profiles. A profile is a series of one or more tasks that a user of the medical device 100 performs. When the medical device 100 operates within a profile, the medical device 100 provides functionality suitable for assisting the user in performing the profile. When the medical device 100 operates within different profiles, the medical device 100 provides different functionality. Some examples of the medical device 100 are configured to be mounted on a mobile cart or on a wall such as the wall of a patient exam room. In other examples, the medical device 100 is a stand-alone device, which can mean that it is not part of a mobile cart and it is not part of a wall-mounted station.

In some embodiments, the medical device 100 is configured to measure one or more physiological parameters of a health-care recipient, also referred to herein as a patient. Various versions of the device 100 are configured more measuring and/or monitoring different parameters and such as temperature, SpO2, blood pressure (NIBP), respiratory rate, etc. Among other things, the user interface 118 is configured to display representations of measurements of the physiological parameters of the patient and to receive commands, instructions, and/or inputs based on interaction of a clinician or user with the user interface 118.

Some examples of the medical device 100 include various monitoring and/or measurement devices that include a plug received by a port 112. A slot 114 provides storage for accessories associated with the particular configuration of the device 100. Thus, the device 100 can be configured to measure and monitor different types of physiological parameters. The device 100 further includes a variety of other configuration settings, such as clinical settings, information settings, data management settings, biomedical settings, etc.

Figure 2:
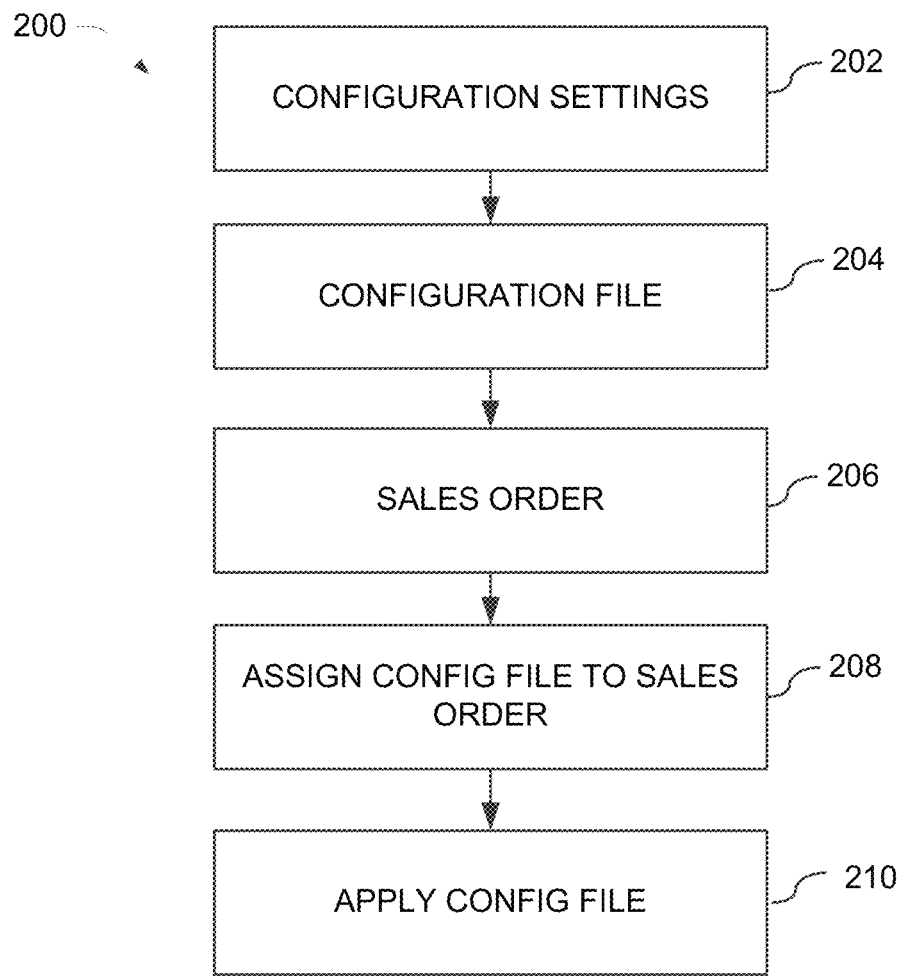
FIG. 2 is a flow diagram illustrating an example of a configuration process in accordance with aspects of the present disclosure.

FIG. 2 is a flow diagram broadly illustrating an example process 200 for configuring a device such as the monitor device 100. In some implementations, the device 100 is configured in accordance with the purchaser's desires, prior to shipping the manufactured device to the use location. For example, in some implementations a customer or potential customer determines desired configuration settings for a device such as the monitor device 100 in block 202 during a pre-sales meeting, and the configuration settings are saved in a configuration file in block 204. A sales order for the device is generated in block 206, and the configuration file is assigned to the sales order in block 208, allowing the configuration file to be retrieved and applied to the device during the manufacturing process in block 210.

In some embodiments, the configuration settings are generated using a web-based configuration application that gathers the configuration settings. Groups of settings may be based on user responses to a smaller, simple set of questions. In this manner, the user can respond to a relatively small number of questions presented in the configuration application, and based on the user responses, a greater number of configuration settings are generated. In an example shown in FIG. 3, a process 300 for determining configuration settings 200 includes a start block 302 and a decision block 304, where a user selects whether to open a new configuration ticket 310, edit an existing ticket 312, or modify a configuration file 314 that includes several configurations. Based on the user selection at block 304, further questions are presented to the user, or predetermined configuration settings could be used based on the user selection.

FIG. 4 illustrates an example process in which the user selected "Open New Ticket" 310 in the process 300 shown in FIG. 3. The new ticket process shown in FIG. 4 begins with a decision block 320 in which the user selects the desired product, then selects the user location in block 324. Depending on whether the product selected at block 320 is to be used in a hospital, office, or long term care location, corresponding configuration settings are presented in blocks 330, 332, and 334 respectively.

FIGS. 5 and 6 illustrate examples of processes for instances where "Edit Open Ticket" and "Modify a Config File," respectively, are selected in decision block 324 of FIG. 3. In FIG. 5, if a valid open ticket number is entered as determined in block 340, the previous configuration process is continued in block 344. In FIG. 6, if a valid configuration file is found in block 350, the relevant previous configuration is continued in block 354.

Figure 7:
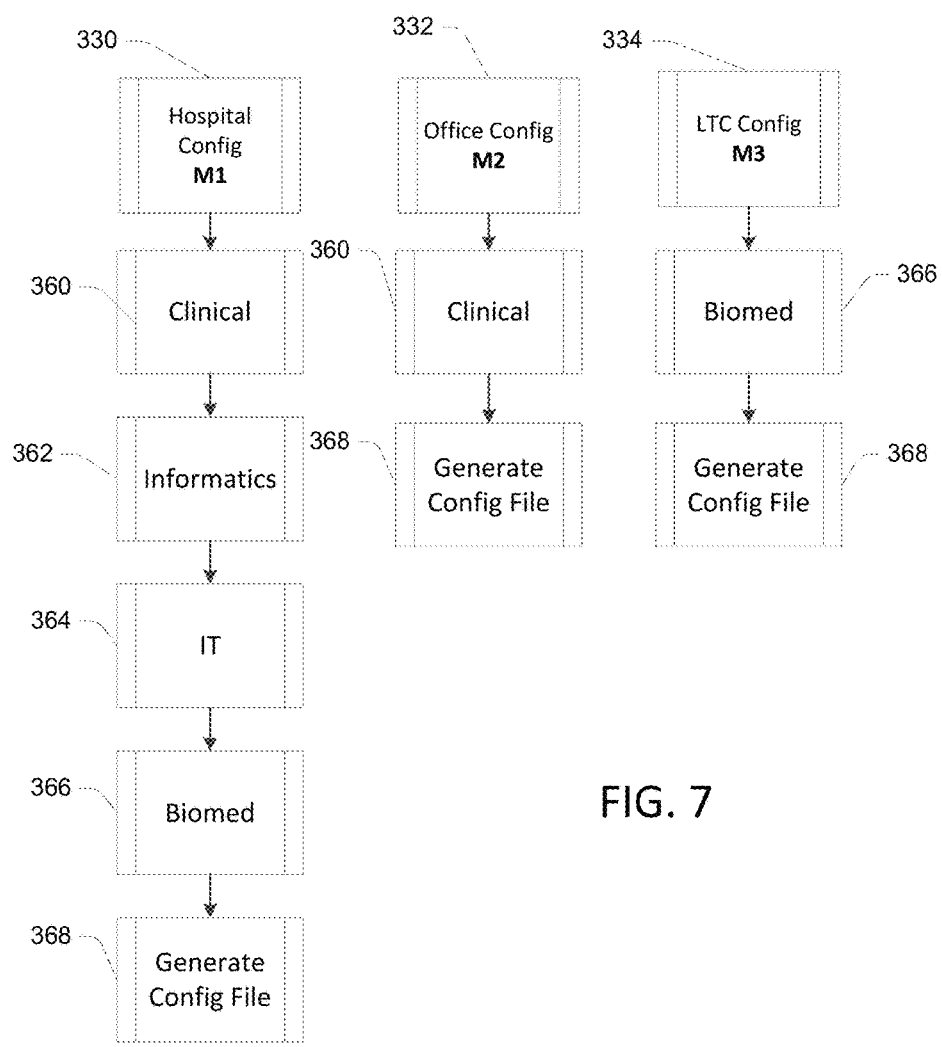
FIG. 7 is a flow diagram illustrating further aspects of the configuration process shown in FIG. 4.

FIG. 7 illustrates further configuration settings associated with the selection of the desired use location as selected in decision block 324 of FIG. 4. Depending on the use location for the device to be configured, further configuration settings are displayed for selection by the user. In the example shown in FIG. 7, if the selected use location is a Hospital 330, configuration settings for clinical 360, informatics 362, and information technology (IT) 364 categories are displayed for selection by the user. The Office selection 332 includes clinical settings 360, and the long term care location 334 includes biomed configuration settings 366. Alternatively, configuration settings in one of more these categories could be predetermined and applied based on the user's responses. Once the configuration settings are determined, the configuration file is generated at block 368 for the respective location.

Figure 8:
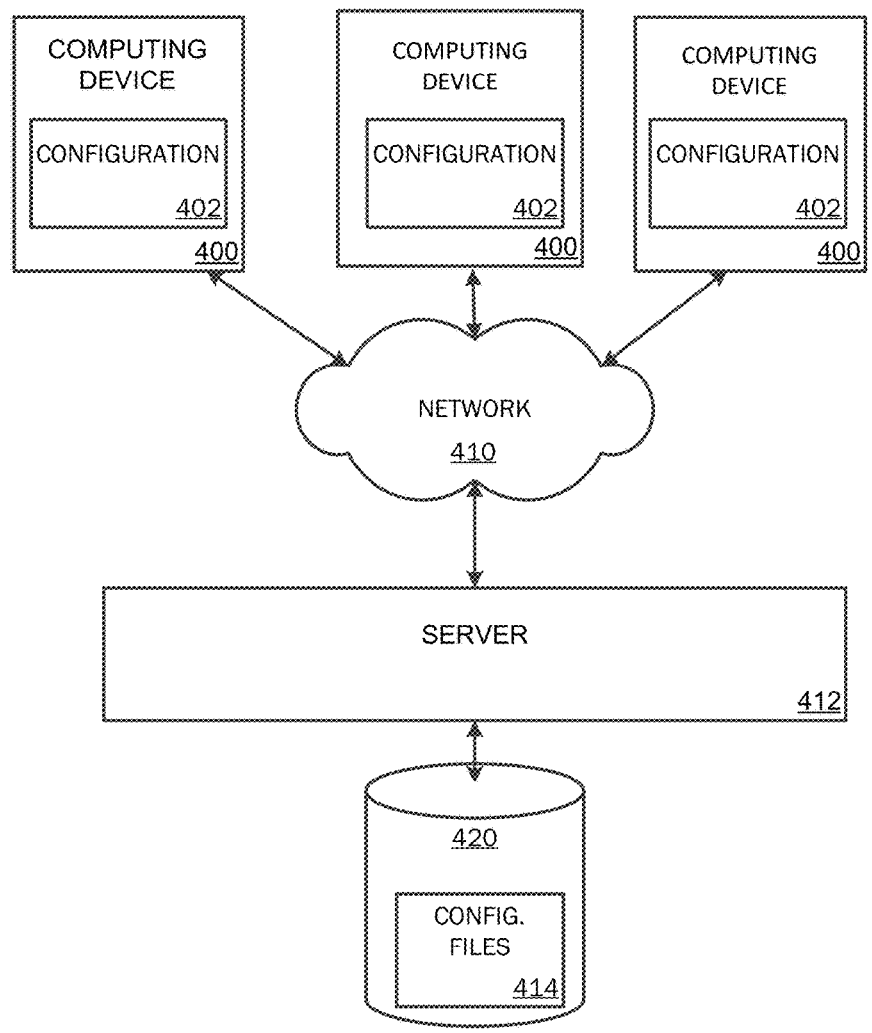
FIG. 8 is a block diagram illustrating an example architecture of a configuration system in accordance with the present disclosure.

As noted above, in some implementations the configuration settings are determined by an end user of the device 100, or by the end user together with a sales person and/or solution architect via a web based configuration application. FIG. 8 illustrates one embodiment of the architecture of a system for processing configuration settings received from a remote source, such as a computing device 400. The computing device 400 contains a configuration application 402 configured to execute processes illustrated and described herein. Configuration files may be stored locally on the computing device 400, stored on portable storage media, and/or sent via a network 410 such as the internet to a server 412 and database 420 that stores the configuration files 414. In this manner, configuration files 414 can be remotely generated, then saved in a central location for later access from a variety of locations.

Figure 9:
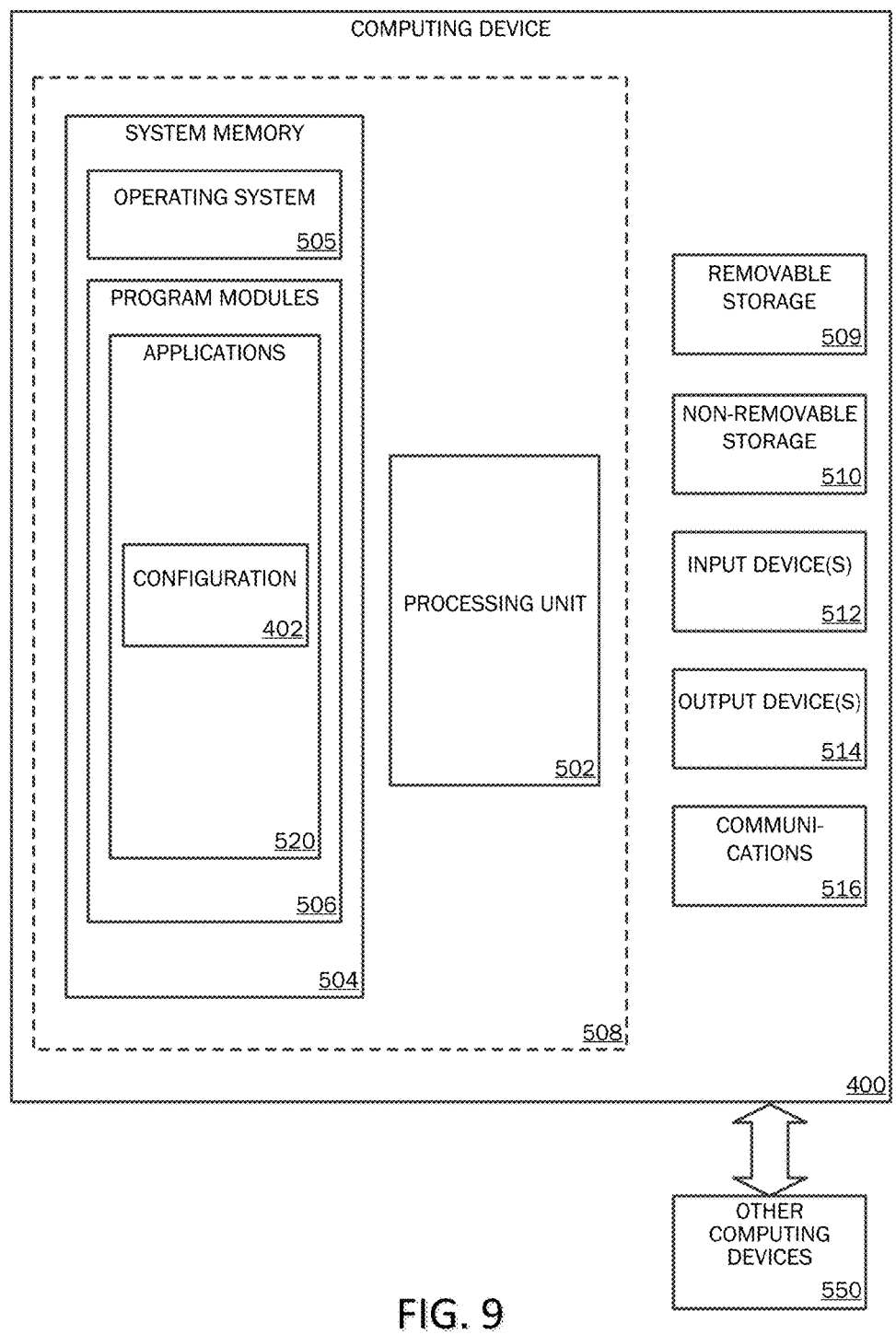
FIG. 9 is a block diagram illustrating an example computing system suitable for running a configuration application in accordance with the present disclosure.

By way of example, the user devices 400 may be embodied in a personal computer, a tablet computing device and/or a mobile computing device (e.g., a smart phone). FIG. 9 illustrates aspects of an example computing device 400 running the configuration application 402. However, the computing device 400 illustrated and discussed with respect to FIG. 9 is for purposes of example and illustration and are not limiting of a vast number of computing device configurations that may be utilized for practicing embodiments of the disclosure, described herein FIG. 9 is a block diagram illustrating physical components (e.g., hardware) of a computing device 400 with which embodiments of the disclosure may be practiced. For example, as noted above the configuration application 402 shown in FIG. 8 could be implemented by the computing device 400. The computing device components described below may include computer executable instructions for a configuration module or application 402 that can be executed to create configuration settings files as disclosed herein. In a basic configuration, the computing device 400 may include at least one processing unit 502 and a system memory 504. Depending on the configuration and type of computing device, the system memory 504 may comprise, but is not limited to, volatile storage (e.g., random access memory), non-volatile storage (e.g., read-only memory), flash memory, or any combination of such memories. The system memory 504 may include an operating system 505 and one or more program modules 506 suitable for running software applications 520 such as the configuration application 402. The operating system 505, for example, may be suitable for controlling the operation of the computing device 400. Furthermore, embodiments of the disclosure may be practiced in conjunction with a graphics library, other operating systems, or any other application program and is not limited to any particular application or system. This basic configuration is illustrated in FIG. 9 by those components within a dashed line 508. The computing device 400 may have additional features or functionality. For example, the computing device 400 may also include additional data storage devices (removable and/or non-removable) such as, for example, magnetic disks, optical disks, or tape. Such additional storage is illustrated in FIG. 9 by a removable storage device 509 and a non-removable storage device 510. For example, configuration settings files could be stored on any of the illustrated storage devices.

As stated above, a number of program modules and data files may be stored in the system memory 504. While executing on the processing unit 502, the program modules 506 (e.g., configuration application 402) may perform processes including, but not limited to, generating configuration files as described herein. Other program modules that may be used in accordance with embodiments of the present disclosure, and in particular to generate screen content, may include electronic mail and contacts applications, word processing applications, spreadsheet applications, database applications, slide presentation applications, drawing, messaging applications, and/or computer-aided application programs, etc.

The computing device 400 may also have one or more input device(s) 512 such as a keyboard, a mouse, a pen, a sound or voice input device, a touch or swipe input device, etc. The output device(s) 514 such as a video display, speakers, a printer, etc. may also be included. The aforementioned devices are examples and others may be used. The computing device 400 may include one or more communication connections 516 allowing communications with other computing devices 518. Examples of suitable communication connections 516 include, but are not limited to, RF transmitter, receiver, and/or transceiver circuitry; universal serial bus (USB), parallel, and/or serial ports.

The term computer readable media as used herein may include computer storage media. Computer storage media may include volatile and nonvolatile, removable and non-removable media implemented in any method or technology for storage of information, such as computer readable instructions, data structures, or program modules. The system memory 504, the removable storage device 509, and the non-removable storage device 510 are all computer storage media examples (e.g., memory storage). Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 400. Any such computer storage media may be part of the computing device 400. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Figure 10:
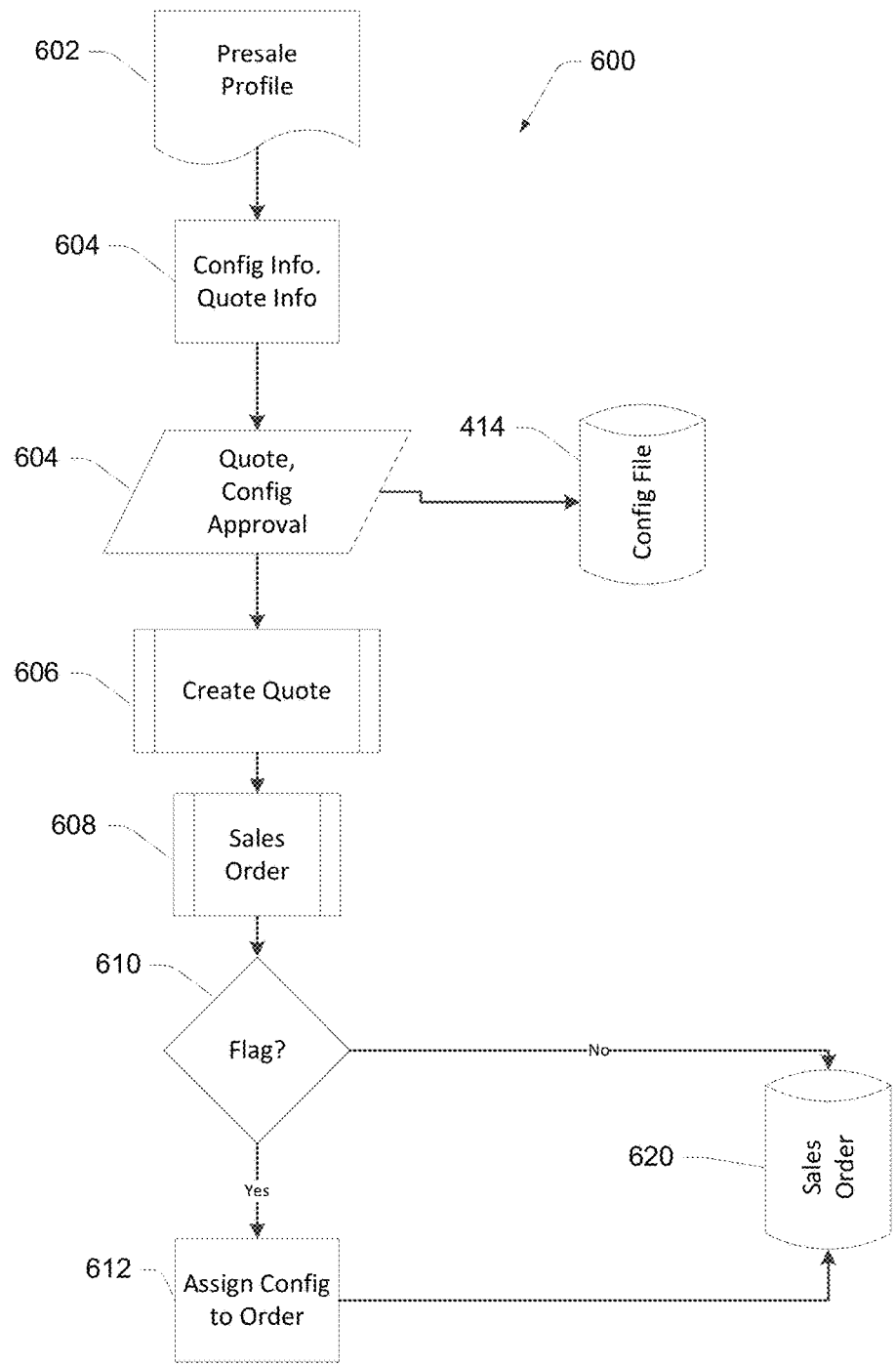
FIG. 10 is a flow diagram illustrating an example of a process for generating a configuration file and sales order in accordance with aspects of the present disclosure.

As noted above, some devices such as the monitor device 100 may be configured for use in a variety of applications in many varied locations and workflows. Since various clinical workflows are often different, providing a configurable device allows a single device to support many different workflows. However, adding such configurability can add complexity. Determining and capturing the desired configuration prior to shipping and installing the device at the use location can simplify the configuration process. FIG. 10 illustrates an example of a presale process 600 in which a sales order for a device is generated. In the illustrated process 600, a presale profile 602 is consulted, for example, during a meeting with a potential purchaser and a sales representative and/or a systems architect. The web-based configuration application 402 and a computing device 400 may be used in the process 600. Configuration information is gathered in block 604, using processes disclosed in conjunction with FIGS. 3-7 in some implementations. If configuration settings are gathered in block 604, the approved configuration file 414 is stored. Approved quote information is used to create a quote in block 606, and when the quote is approved a sales order is generated in block 608.

If the sales order includes a device to be configured during the manufacturing process, the sales order is flagged to identify it as requiring configuration. In some implementations, this includes adding a generic part number to a line item in the sales order at block 608. At a decision block 610, if it is determined that the sales order 608 does not include the flag (no custom configuration is required), the sales order is saved as indicated at item 620. If the sales order 608 includes the flag identifying the order as requiring configuration, the configuration information is associated with the sales order at block 612, and the sales 620 is saved.

Figure 11:
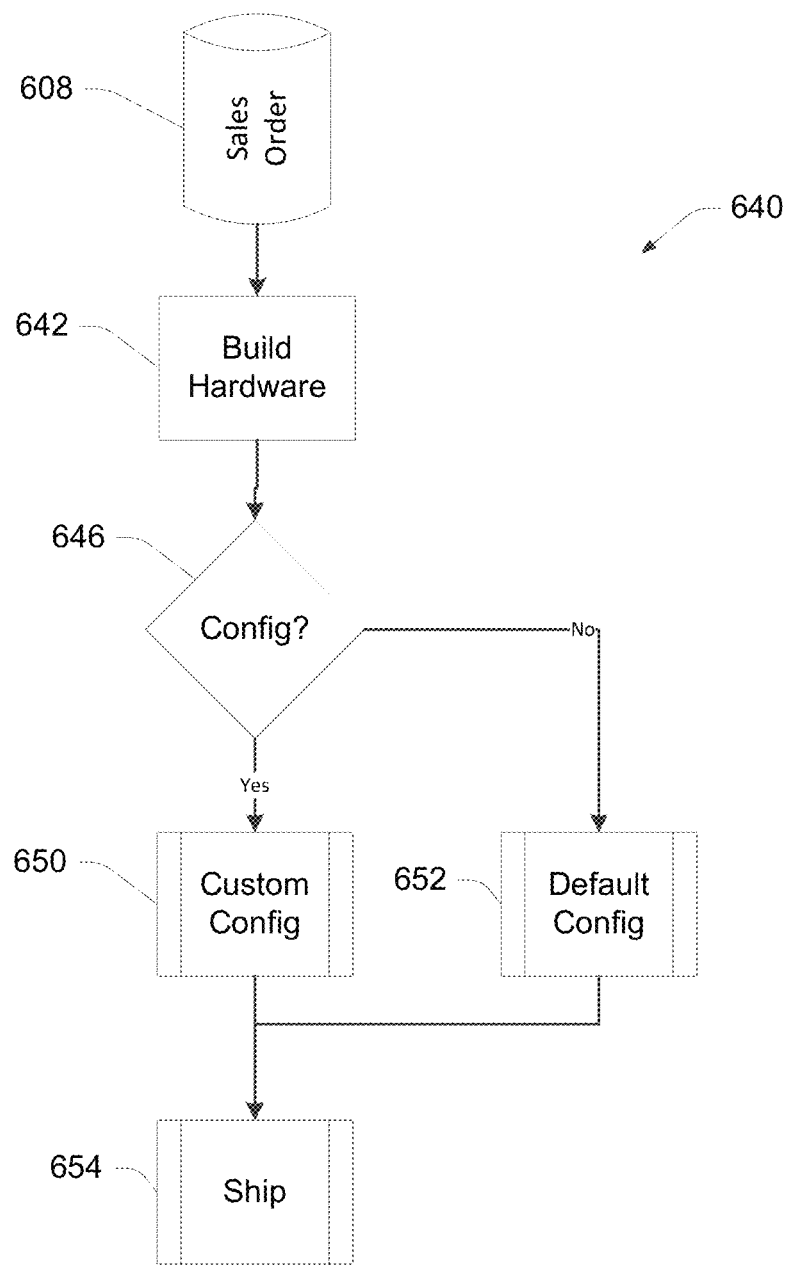
FIG. 11 is a flow diagram illustrating an example of a manufacturing process for applying configuration settings to a device in accordance with aspects of the present disclosure.

FIG. 11 illustrates portions of an example of a manufacturing process in which a configuration file is applied to a device during the manufacturing process, allowing a configured device to be shipped to the customer. At bock 642 the sales order 608 is retrieved and device hardware is built per the sales order 608. In some implementations, a manufacturing "traveler" is created that accompanies the device through the manufacturing process. The traveler includes, for example, the sales order number, sales order items, customer number, customer name, configuration file identification, etc. At a decision block 646, the sales order 608 is reviewed and if is determined that the sales order 608 requires a custom configuration, the manufactured device is configured using the configuration file 414 at block 650. If the sales order 608 does not require a custom configuration, a default configuration may be loaded into the device at block 652. At block 654, the manufactured device is shipped to the customer.

The processes disclosed in conjunction with FIGS. 10 and 11 allow, among other things, assigning individual custom configuration files to line items within a sales order. This allows, for example, multiple devices to be built having the same hardware configuration, yet different software configurations. Referring back to FIG. 10, the sales order 608 created could include several of the devices 100. The customer may desire to have different devices configured differently.

Figure 12:
FIG. 12 illustrates a first screen shot from an example of a configuration tool in accordance with aspects of the present disclosure.

FIGS. 12-17 illustrate examples of screen shots from an on-line configuration application in accordance with aspects of the present disclosure. The illustrated screen shots may be displayed on an output device 514 such as a video display monitor of the computing device 400 illustrated in FIG. 9, for example. User inputs may be received via any suitable input device(s) 512, such as those discussed in conjunction with the description of FIG. 9 herein above. FIG. 12 shows an example "dashboard" screen 700 in which user choices include list configurations 701, new configuration 702, and assign configuration 703. FIG. 12 illustrates the dashboard for a "Monitor Device" 704 with list configurations 701 selected. Accordingly, a configurations list is displayed in which various configurations 706 are listed, along with creation and update dates/times for each configuration 706. For each of the configurations 706 listed, options for edit 710, copy 711, delete 712 and download 713 functions are displayed. The new configuration 702 option allows a user to create a new configuration, and the assign configuration 703 option allows a user to assign a configuration to a line item of a sales order.

Figure 13:
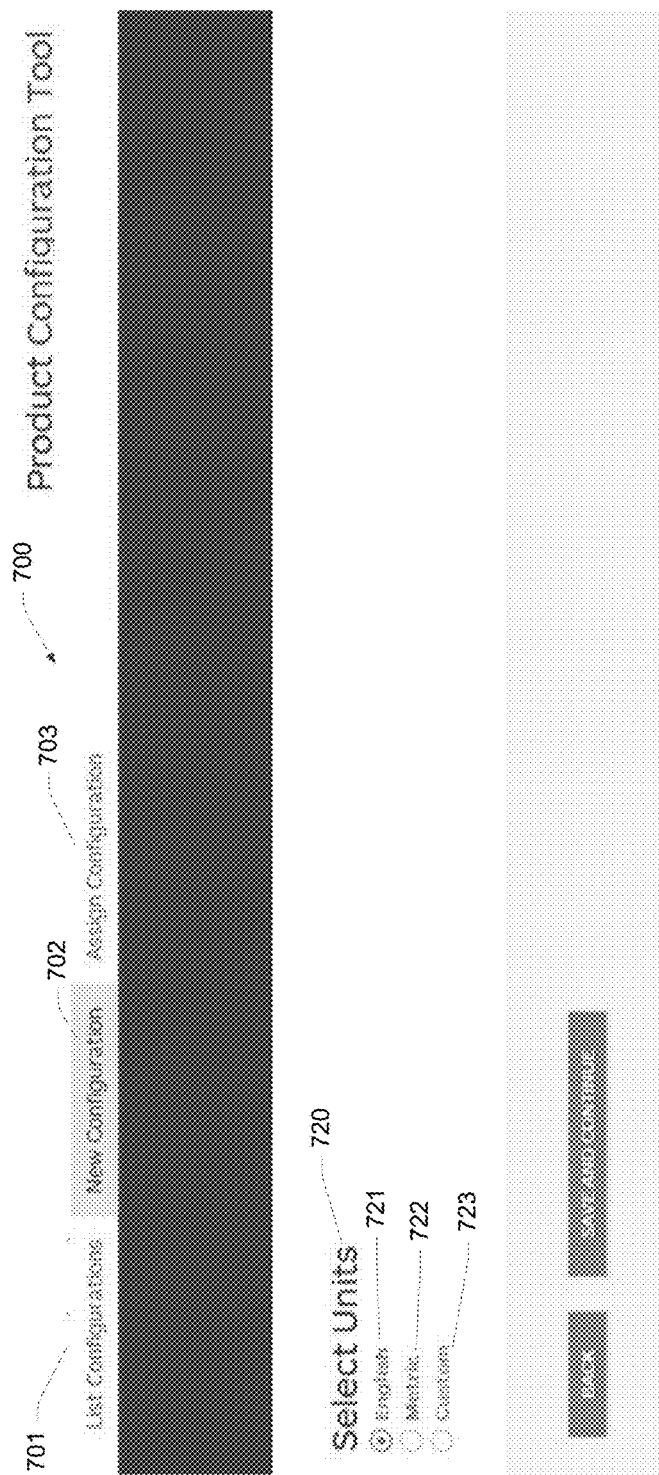
FIG. 13 illustrates a second screen shot from an example of a configuration tool in accordance with aspects of the present disclosure.

FIG. 13 illustrates an example of the dashboard screen 700 in which the new configuration 702 option has been selected, wherein a new configuration file is created for the desired device. In some examples, configuration settings are determined by a user and saved in a configuration file, such as an XML file. As noted in the disclosure above in conjunction with FIG. 7, further questions or options are presented to the user based on earlier user selections in the configuration process, or predetermined configuration settings are used based on the user selections. In an example of the configuration creation process, the user selects desired units 720, which include English 721, Metric 722 and Custom 723 measurement units in the illustrated screen. In the example shown in FIG. 13, English units 721 have been selected. In response to this selection, appropriate predetermined English measurement units for various measured parameters are saved in the configuration file.

Figure 14:
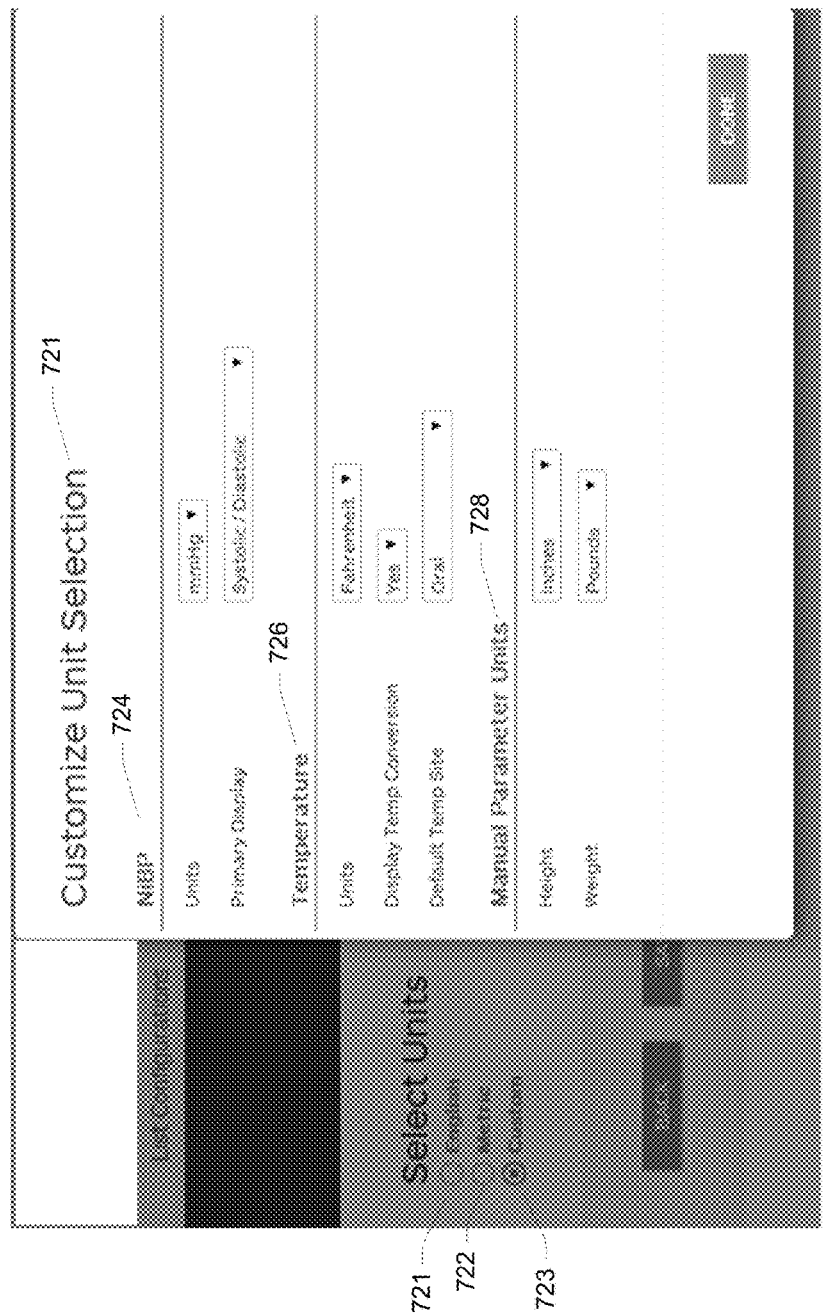
FIG. 14 illustrates a third screen shot from an example of a configuration tool in accordance with aspects of the present disclosure.

FIG. 14 illustrates a screen shot where the Custom measurement units option 723 has been selected. In this case, for various monitored parameters such as blood pressure 724, temperature 726 and manual parameter units 728 are displayed, and the user may select the desired measurement units for the various parameters.

Figure 15:
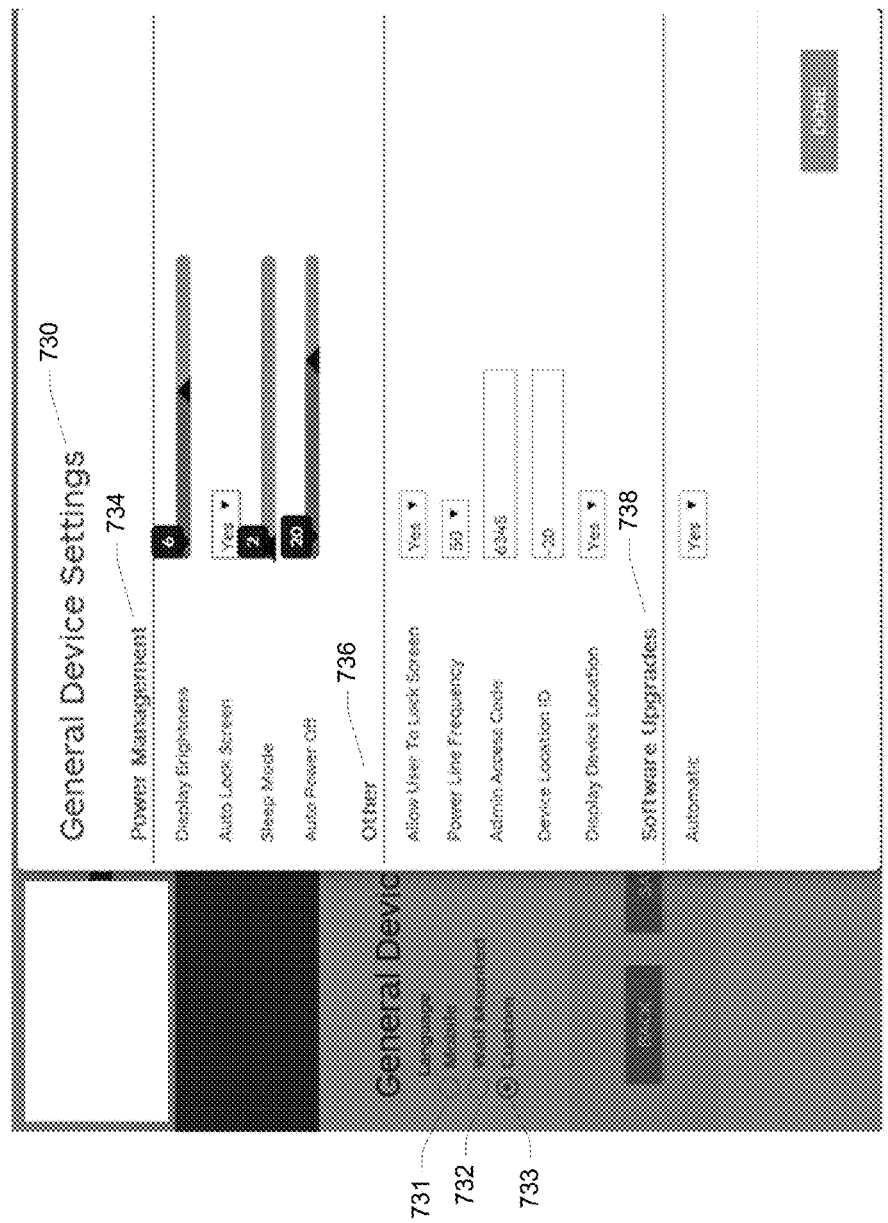
FIG. 15 illustrates a fourth screen shot from an example of a configuration tool in accordance with aspects of the present disclosure.

As noted earlier in conjunction with the description of the device 100 illustrated in FIG. 1, examples of the medical device 100 are configured to be mounted on a mobile cart or on a wall such as the wall of a patient exam room. In other examples, the medical device 100 is a stand-alone device, which can mean that it is not part of a mobile cart and it is not part of a wall-mounted station. FIG. 15 illustrates a configuration screen 730 displaying general device options including mobile 731, wall mounted 732 and custom 733. If the user selects mobile 731 or wall mounted 732, preset device settings for the respective device configurations are included in the created configuration for the device. FIG. 15 illustrates a configuration screen 730 in which the custom option 733 has been selected. For the custom option 733, the user may select among various choices corresponding to various categories, including power management 734, other 736 and software upgrades 738 in the illustrated example. The selected choices are included in the configuration file for the device.

Figure 16:
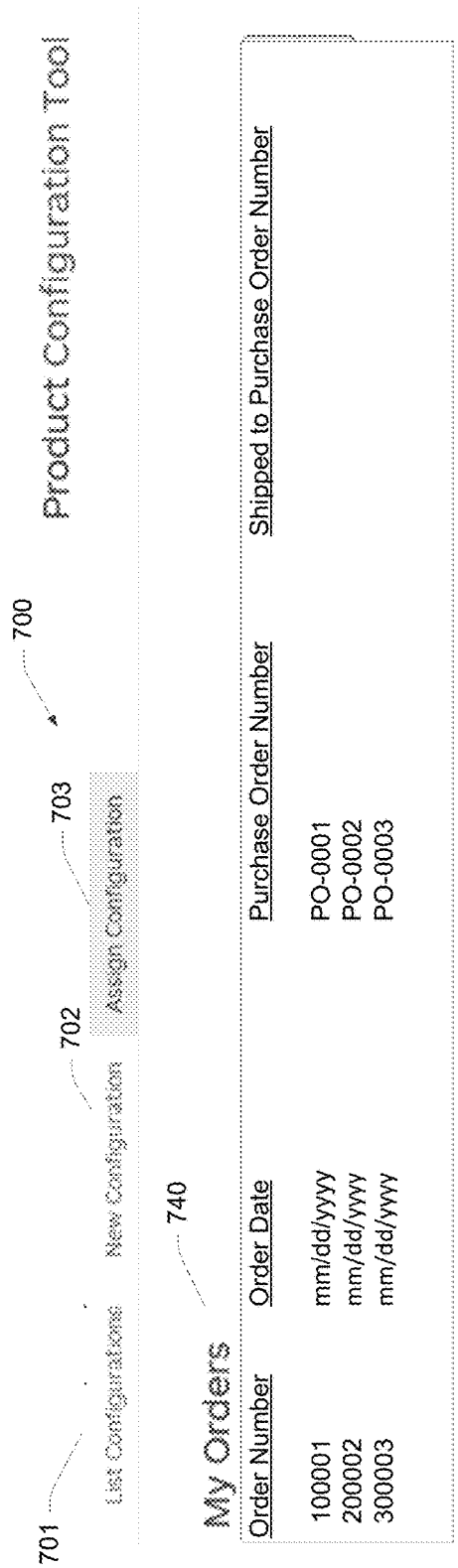
FIG. 16 illustrates a fifth screen shot from an example of a configuration tool in accordance with aspects of the present disclosure.

FIG. 16 illustrates an example of the dashboard screen 700 where the assign configuration option 703 has been selected. In some embodiments, selection of this option causes the configuration tool to communicate with a sales or order-entry system including the database 620 in which sales orders 608 are stored. The database 620 is queried and orders 740 for the logged-in user are displayed. In the example shown in FIG. 16, a query of the database 620 is conducted to identify open and flagged orders, such that open orders requiring assignment of configurations are displayed.

Figure 17:
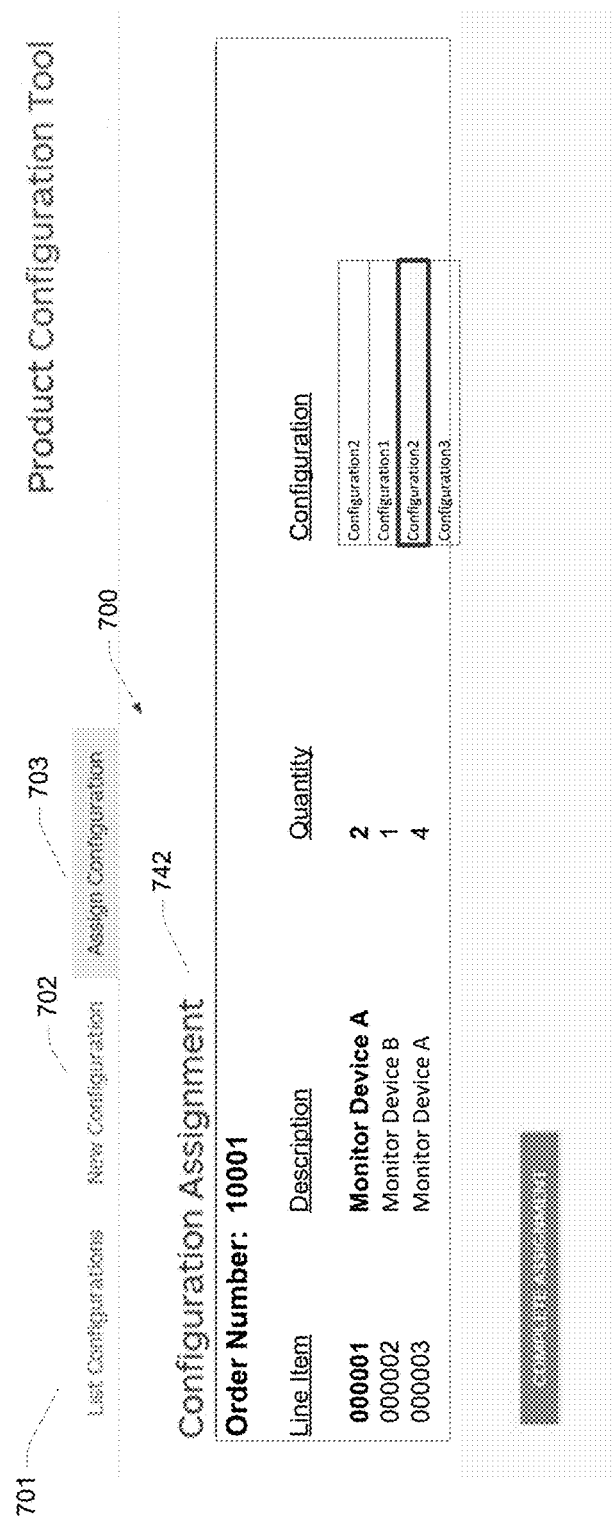
FIG. 17 illustrates a sixth screen shot from an example of a configuration tool in accordance with aspects of the present disclosure.

FIG. 17 illustrates an example where the first order number, 100001 has been selected in the previous screen shown in the example of FIG. 16. In FIG. 17, the line items for the selected order number are displayed. In the illustrated example, line item 00001 has been selected by the user and available configurations for the selected line item are displayed. In the example shown in FIG. 17, Configuration2 has been selected to be assigned to line item 000001 of order number 10001. The user may select a desired configuration for each line item in the selected order that requires a custom configuration. In this manner, a sales order that includes several devices listed as line items in the sales order can have desired configurations assigned thereto. Even if the same type or model of hardware device is listed in multiple line items (note "Monitor Device A" is listed in line items 000001 and 000003 in FIG. 17), these hardware devices can have different configurations applied thereto. For example, the customer may be purchasing a quantity of two Device A (line items 00001 and 000003), but these identical hardware devices are to be located in different wings of a clinic, and therefore require different configurations. Rather than requiring the end user to configure the devices, the devices can be shipped to the customer with the desired respective configurations loaded at the factory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

The description and illustration of one or more embodiments provided in this application are not intended to limit or restrict the scope of the disclosure as claimed in any way. The embodiments, examples, and details provided in this application are considered sufficient to convey possession and enable others to make and use the best mode of claimed disclosure. The claimed disclosure should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed disclosure.

The invention claimed is:

1. A method for configuring a vital signs monitor device, comprising:
   determining a plurality of configuration settings for the vital signs monitor device, the plurality of configuration settings including:
   location settings defining a clinical location at which the vital signs monitor device will be used; and
   one or more clinical workflows for the vital signs monitor device associated with the clinical location, wherein the one or more clinical workflows provide different functionalities of the vital signs monitor device;

saving the configuration settings in a configuration file;

generating a sales order for the vital signs monitor device;

assigning the configuration file to the sales order; and applying the configuration settings to the vital signs monitor device.

2. The method of claim 1, further comprising retrieving the configuration file based on a sales order number of the sales order.

3. The method of claim 1, further comprising assigning the configuration file to a line item of the sales order.

4. The method of claim 1, further comprising saving the configuration settings in a plurality of configuration files.

5. The method of claim 1, further comprising:

saving the configuration settings in a plurality of configuration files; and assigning the plurality of configuration files to a plurality of line items of the sales order.

6. The method of claim 1, wherein determining the plurality of configuration settings includes receiving responses to a plurality of predetermined questions.

7. The method of claim 6, wherein receiving responses to a plurality of predetermined questions includes receiving responses to a first number of predetermined questions, wherein a second number of configuration settings are determined in response to the first number of responses, and wherein the second number is greater than the first number.

8. The method of claim 1, wherein the plurality of configuration settings are determined before generating a sales order.

9. The method of claim 1, wherein the plurality of configuration settings are determined after generating the sales order.

10. The method of claim 1, further comprising modifying the configuration settings after the configuration settings have been saved in the configuration file.

11. The method of claim 1, further comprising flagging the sales order in response to assigning the configuration file to the sales order.

12. A computer storage medium including instructions that when executed by a computing system perform a method for configuring a device, comprising:

determining a plurality of configuration settings for a vital signs monitor device, the configuration settings including:

clinical settings identifying a location for the vital signs monitor device, the location being one of hospital, office, or long term care; and one or more clinical workflows for the vital signs monitor device associated with the selected location, wherein the one or more clinical workflows provide different functionalities of the vital signs monitor device;

saving the configuration settings in a configuration file;

generating a sales order for the vital signs monitor device;

assigning the configuration file to the sales order; and applying the configuration settings to the vital signs monitor device.

\* \* \* \* \*